United States Patent [19]
Bru-Magniez et al.

[11] Patent Number: 5,459,132
[45] Date of Patent: Oct. 17, 1995

[54] N6-[(IMIDAZO[1,2-A]PYRIDIN-3-YL)ETHYL] ADENOSINES, THEIR 5'-URONAMIDE ANALOGUES AND PHARMACEUTICAL COMPOSITIONS

[75] Inventors: Nicole Bru-Magniez, Paris; Timur Güngor, Rueil Malmatson; Jean-Marie C. Teulon, La Celle Saint Cloud, all of France

[73] Assignee: Laboratoires UPSA, Agen, France

[21] Appl. No.: 196,454

[22] Filed: Feb. 15, 1994

[30] Foreign Application Priority Data

Jan. 7, 1994 [FR] France .................... 94 00108

[51] Int. Cl.⁶ .................... A61K 31/70; C07H 19/167
[52] U.S. Cl. .................... 514/46; 536/27.22; 536/27.11; 536/27.62; 536/27.63
[58] Field of Search ............ 536/27.22, 27.11, 536/27.62, 27.63; 514/46

[56] References Cited

U.S. PATENT DOCUMENTS

| | | | |
|---|---|---|---|
| 4,853,386 | 8/1989 | Friebe et al. | 514/266 |
| 4,954,504 | 9/1990 | Chen et al. | 514/265 |
| 5,055,569 | 10/1991 | Becker et al. | 514/46 |
| 5,217,982 | 6/1993 | Fink et al. | 514/352 |
| 5,229,505 | 7/1993 | Bru-Magniez et al. | 536/27.62 |

FOREIGN PATENT DOCUMENTS

| | | | |
|---|---|---|---|
| 0423776 | 4/1991 | European Pat. Off. | 514/46 |
| 0423777 | 4/1991 | European Pat. Off. | 514/46 |
| 9205177 | 4/1992 | WIPO | 514/46 |

OTHER PUBLICATIONS

Daly, "Adenosine Receptors: Targets for Future Drugs," *J. Med. Chem.*, 25(3), 197–207 (1982).
Jacobsen et al. "Adenosine Receptors: Pharmacology, Structure–Activity Relationships, and Therapeutic Potential," *J. Med. Chem.* 35(3), 407–422 (1992).
Daly et al., "Structure–Activity Relationships for $N^6$–Substituted Adenosines at a Brain at a Brain $A_1$–Adenosine Receptor with a Comparison to an $A_2$–Adenosine Receptor Regulating Coronary Blood Flow," *Biochemical Pharmacology*, 35(15), 2467–2481 (1986).
Levitzki, "Tyrphostins: Tyrosine Kinase Blockers as Novel Antiproliferative Agents and Dissectors of Signal Transduction," *FASEB J.*, 6, 3277–3282 (1992).

*Primary Examiner*—Douglas W. Robinson
*Assistant Examiner*—L. Eric Crane
*Attorney, Agent, or Firm*—Dennison, Meserole, Pollack & Scheiner

[57] ABSTRACT

The present invention relates to the derivatives of the formula

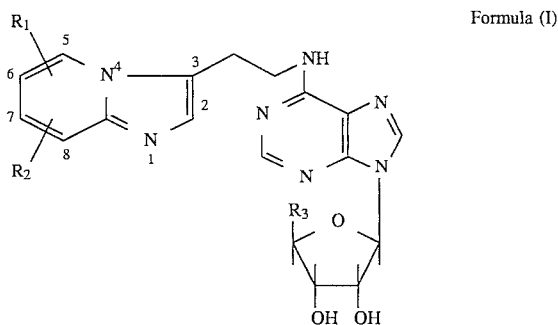

Formula (I)

and their addition salts, and to their use in therapeutics as analgesics, as antihypertensives and as drugs with antiproliferative properties.

9 Claims, No Drawings

N6-[(IMIDAZO[1,2-A]PYRIDIN-3-YL)ETHYL] ADENOSINES, THEIR 5'-URONAMIDE ANALOGUES AND PHARMACEUTICAL COMPOSITIONS

The present invention relates, by way of novel products, to the adenosine derivatives of general formula (I) below and their addition salts, in particular the pharmaceutically acceptable addition salts.

The compounds in question have a very valuable pharmacological profile insofar as they possess anti-proliferative properties, and can advantageously be used in therapeutics in the treatment of cancer, psoriasis, atherosclerosis, restenosis phenomena or any other pathological condition due to cell proliferation in mammals and in particular in man.

Furthermore, the compounds in questions also possess on the one hand analgesic properties in particular, and on the other hand antihypertensive properties.

The present invention further relates to the method of preparing said products, to the synthesis intermediates and to the application of these products in therapeutics.

These adenosine derivatives have general formula (I):

Formula (I)

in which:

$R_1$ and $R_2$ can be located in the 2-, 5-, 6-, 7- or 8-position of the imidazopyridine and independently are:
the hydrogen atom,
a lower alkyl radical having 1 to 6 carbon atoms,
a halogen atom,
a radical $O—(CH_2)_n—R_4$,
in which n is an integer from 0 to 5 and $R_4$ is the hydrogen atom, a lower alkyl radical having 1 to 6 carbon atoms, a $C_3$–$C_7$-cycloalkyl radical, a lower O-alkyl radical having 1 to 6 carbon atoms, a phenyl radical which is unsubstituted or substituted by one to four identical or different substituents selected from a halogen atom or a lower alkyl radical having 1 to 6 carbon atoms, or a pyridyl radical, or
a phenyl radical; and $R_3$ is:
a group —CO—NHR$_5$,
in which $R_5$ is a lower alkyl radical having 1 to 6 carbon atoms, a $C_3$–$C_7$-cycloalkyl radical, a radical —(CH$_2$)$_m$—OR$_6$ or a radical —(CH$_2$)$_m$—NR$_7$R$_8$, in which m is an integer from 2 to 5, $R_6$ is the hydrogen atom or a lower alkyl radical having 1 to 6 carbon atoms and $R_7$ and $R_8$ simultaneously are a lower alkyl radical having 1 to 6 carbon atoms or form, together with the nitrogen atom to which they are attached, a heterocycle selected from morpholine, piperidine or pyrrolidine, or
a group CH$_2$ OH.

Advantageously, the derivatives according to the invention are the derivatives of formula (I) given above in which:

$R_1$ and $R_2$, which can be located in the 2- or 8-position of the imidazopyridine, independently are:
the hydrogen atom,
a lower alkyl radical having 1 to 6 carbon atoms,
a halogen atom or
a radical $O—(CH_2)_n—R_4$,
in which n is an integer from 0 to 2 and $R_4$ is a lower alkyl radical having 1 to 6 carbon atoms, a $C_3$–$C_7$-cycloalkyl radical, a lower O-alkyl radical having 1 to 6 carbon atoms or a phenyl radical which is unsubstituted or substituted by one or two lower alkyl radicals having 1 to 6 carbon atoms; and $R_3$ is:
a group —CO—NHR$_5$,
in which $R_5$ is a lower alkyl radical having 1 to 6 carbon atoms, a $C_3$–$C_7$-cycloalkyl radical, a radical —CH$_2$—CH$_2$—O—R$_6$, in which $R_6$ is a lower alkyl radical having 1 to 6 carbon atoms, or a 2-morpholinoethyl radical, or
a group —CH$_2$OH.

In the description and the claims, lower alkyl radical is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

$C_3$–$C_7$-Cycloalkyl radical is understood as meaning a saturated cyclic radical, preferably a cyclopropyl, cyclobutyl, cyclopentyl, cyclohexyl or cycloheptyl radical.

Halogen is understood as meaning a chlorine, bromine, iodine or fluorine atom.

In view of the therapeutic potential of adenosine itself, numerous derivatives of this nucleoside have been described in the literature. The following documents may be cited as examples:

J. Med. Chem. 1982, 25, 197–207,
Biochem. Pharm. 1986, 35, 2467–2481,
J. Med. Chem. 1992, 35, 407–422, and
Current Cardiov. Patents 1989, 1, 560–576.

The most widely known effects of adenosine derivatives relate most frequently to the cardiovascular system. It is only very recently that the emphasis has shifted to the possibility of acting on spinal pain via an adenosinergic mechanism, with the difficulty of obtaining non-toxic products active by the oral route.

Now, the Applicant has discovered that, surprisingly and unexpectedly, the use of imidazo[1,2-a]pyridine substituents in the N$^6$-position of adenosine, on its own or combined with conversion of the primary alcohol of the sugar to an amide group, gives the products a particularly valuable pharmacological profile, not only in the field of analgesia but also in the field of inhibition of cell proliferation.

Advantageously, within the framework of the present invention, a compound of formula (I) will be used in which at least one of the following conditions is satisfied:

$R_1$ is the phenylmethoxy group,
$R_1$ is the (2,5-dimethylphenyl)methoxy group,
$R_1$ is the 2-methoxyethoxy group,
$R_1$ is the cyclopentoxy group,
$R_1$ is the isopropoxy group,
$R_2$ is the hydrogen atom,
$R_2$ is a methyl radical and
$R_3$ is an N-cyclopropylcarboxamide radical.

The particularly preferred compounds of the invention are selected from the derivatives of the formulae

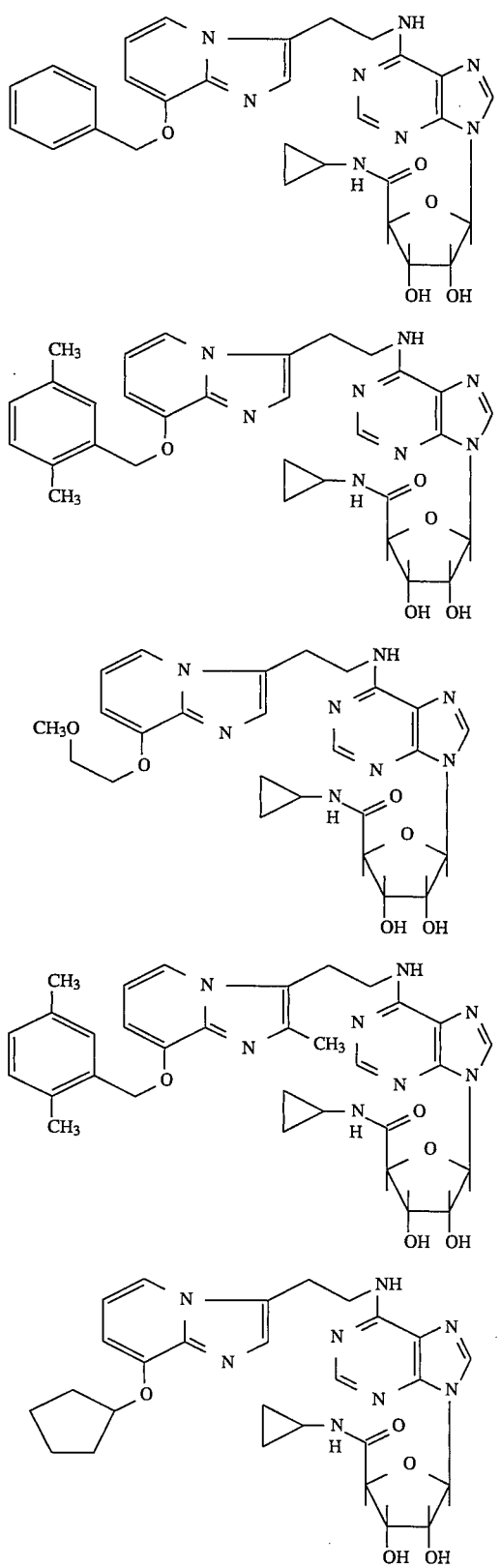

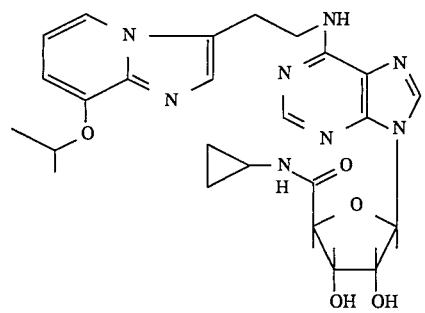

According to the invention, the compounds of formula (I) may be synthesized in the following manner:

Reaction of an amine of formula (II):

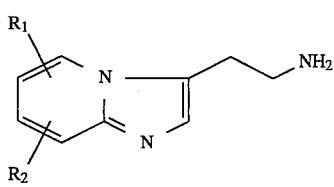

Formula (II)

in which $R_1$ and $R_2$ are as defined above, with the 6-halogenopurine ribosides of formula (III):

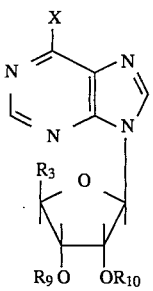

Formula (III)

in which X is a halogen atom, preferably chlorine or bromine, $R_3$ is as defined above and $R_9$ and $R_{10}$ are protecting groups for the alcohol functional group, such as, for example, an acetyl, a benzoyl or a benzyl, or can together form another protecting group, for example of the dioxolan structure, in a solvent such as, for example, an alcohol or an aprotic solvent such as dimethylformamide, in the presence of a base such as triethylamine, pyridine or sodium, potassium or calcium carbonate, or else in the presence of two equivalents of the amine of formula (II), at a temperature of between 20° and 140° C., will give the compounds of formula (IV):

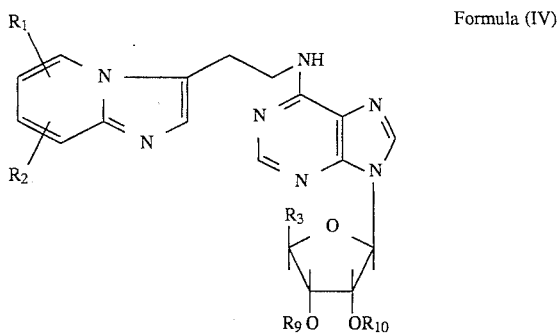

Formula (IV)

in which $R_1$, $R_2$, $R_3$, $R_9$ and $R_{10}$ are as defined above.

In the case where the radical $R_3$ is the group $CH_2OH$, it may be oxidized to the acid for example with:

chromic anhydride by the method described by:
R. R. SCHMIDT and H. J. FRITZ, Chem. Ber. 1970, 103, 1867, or potassium permanganate in the presence of aqueous ammonia by the method described by:
P. J. HARPER and A. HAMPTON, J. Org. Chem. 1970, 35, no. 5, 1688, or the system $RuCl_3/NaIO_4$ by the method described by:
A. K. SINGH and R. S. VARMA, Tet. Lett. 1992, 17, 2307. The resulting ribouronic acid is converted to the acid chloride by reaction with thionyl chloride, for example, and then to an amide by reaction with an amine by the methods known to those skilled in the art. Deprotection of the secondary alcohols $OR_9$ and $OR_{10}$ may be carried out by different methods, for example in a basic medium such as ammoniacal alcohol, or in an acid medium such as a normal hydrochloric acid solution or a formic acid solution, at temperatures varying from 0° to 70° C. depending on the nature of the protecting groups.

These reaction sequences make it possible to convert the derivatives of formula (IV) to derivatives of formula (I).

The compounds of formula (II) can be obtained from imidazo[1,2-a]pyridine compounds unsubstituted in the 3-position, of formula (V):

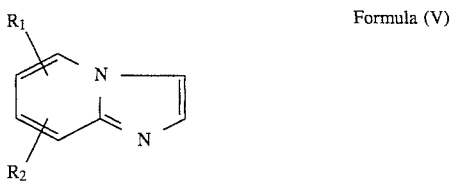

Formula (V)

in which $R_1$ and $R_2$ are as defined above, either by means of a Vilsmeier-Haack reaction followed by condensation with nitromethane in the presence of ammonium acetate to give derivatives of formula (VI):

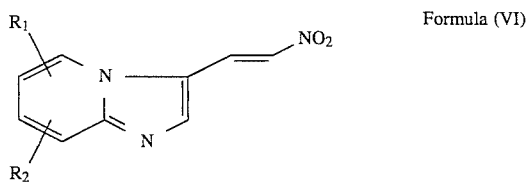

Formula (VI)

in which $R_1$ and $R_2$ are as defined above, these derivatives then being reduced by catalytic hydrogenation in the presence of Raney nickel or with lithium aluminum hydride to give the compounds of formula (II), or by means of a Mannich reaction with dimethylamine and then the formation of quaternary trimethylammonium salts, followed by substitution with the group CN by reaction with a cyanide to give the compounds of formula (VII):

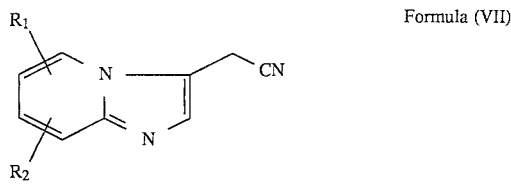

Formula (VII)

in which $R_1$ and $R_2$ are as defined above, these derivatives then being reduced by catalytic hydrogenation in the presence of Raney nickel and ammonia or with lithium aluminum hydride to give the compounds of formula (II).

The imidazo[1,2-a]pyridine compounds of formula (V) are described in the literature or can be prepared by the conventional methods described especially by:
H. L. BLEWITT in Special Topics in Heterocyclic Chemistry; A. WEISSBERGER, E. C. TAYLOR, eds.; Wiley, New York, 1977, p. 117, and more recently by:
J. A. KAMINSKI et al., J. Med. Chem. 1985, 28, 876–892.

The most common method consists in reacting 2-aminopyridine derivatives of formula (VIII):

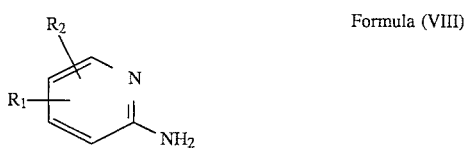

Formula (VIII)

in which $R_1$ and $R_2$ are as defined above, with α-halogenocarbonyl compounds.

In the case where the carbonyl compounds are asymmetrical, two imidazo[1,2-a]pyridines can be obtained, the structure of which is determined by conventional methods of identification in organic chemistry.

The compounds of formula (VIII) can be obtained by various methods described in the literature, depending on the nature of the substituents $R_1$ and $R_2$ as defined above. Processes which will be used are for example those described in the following literature references:
J. Org. Chem. 1970, 35, 4254–4256, and
Synthesis 1981, 971–973.

The 6-halogenopurines of formula (III) are prepared from inosine by methods described in the following literature:
R. R. SCHMIDT and H. J. FRITZ, Chem. Ber. 1970, 103, 1867,
H. M. KISSMAN and M. J. WEISS, J. Org. Chem. 1956, 21, 1053,
B. R. BAKER, K. HEWSON, H. J. THOMAS and J. A. JOHNSON JR, J. Org. Chem. 1957, 22, 954, and
J. ZEMLICKA and F. SORM, Coll. Czech. Chem. Commun. 1965, 30, (6), 1880.

The compounds of formula (I) as defined above, and their addition salts, in particular the pharmaceutically acceptable addition salts, possess a good affinity for adenosine receptors. This affinity gives them a good analgesic activity but also antihypertensive properties. Furthermore, the Applicant has demonstrated that these compounds of formula (I) possess a good anti-proliferative activity.

These properties justify the application of the derivatives of formula (I) in therapeutics and the invention further relates, by way of drugs, to the products as defined by formula (I) above, and their addition salts, in particular the pharmaceutically acceptable addition salts.

Thus the invention also covers a pharmaceutical composition which comprises a pharmaceutically effective amount of at least one compound of formula (I) as defined above, or one of its pharmaceutically acceptable addition salts, which may or may not be incorporated in a pharmaceutically acceptable excipient, vehicle or carrier.

These compositions can be administered by the buccal, rectal, parenteral, transdermal or ocular route.

These compositions can be solid or liquid and can take the pharmaceutical forms commonly used in human medicine, such as, for example, simple or coated tablets, gelatin capsules, granules, suppositories, injectable preparations, transdermal systems and eye lotions. They are prepared by the customary methods. The active principle, which consists of a pharmaceutically effective amount of at least one compound of formula (I) as defined above, or one of its pharmaceutically acceptable addition salts, can be incorporated therein with excipients normally employed in these pharmaceutical compositions, such as talc, gum arabic, lactose, starch, magnesium stearate, polyvidone, cellulose derivatives, cacao butter, semisynthetic glycerides, aqueous or non-aqueous vehicles, fatty substances of animal or vegetable origin, glycols, various wetting agents, dispersants or emulsifiers, silicone gels, certain polymers or copolymers, preservatives, flavorings and colors.

The invention also covers a pharmaceutical composition with analgesic activity affording especially a favorable treatment for pain, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a pharmaceutical composition with antihypertensive activity affording a favorable treatment for hypertension, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a pharmaceutical composition with anti-proliferative activity affording especially a favorable treatment for any pathological condition due to cell proliferation, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. In one embodiment, a pharmaceutical composition with analgesic activity is prepared which affords especially a favorable treatment for pain; in another embodiment, a pharmaceutical composition with antihypertensive activity is prepared which affords especially a favorable treatment for hypertension; in another embodiment, a pharmaceutical composition with anti-proliferative activity is prepared which affords especially a favorable treatment for cancer, psoriasis, atherosclerosis, restenosis phenomena or any other pathological condition due to cell proliferation.

In another variant, a pharmaceutical composition is formulated as gelatin capsules or tablets containing from 1 to 1000 mg of active ingredient, or as injectable preparations containing from 0.1 mg to 500 mg of active ingredient. Formulations as suppositories, ointments, creams, gels, aerosol preparations or eye lotions may also be used.

The invention also covers a method of therapeutic treatment for mammals, which comprises administering to this mammal a therapeutically effective amount of at least one compound of formula (I) as defined above, or one of its pharmaceutically acceptable addition salts. In one variant of this method of treatment, the compound of formula (I), either by itself or in association with a pharmaceutically acceptable excipient, is formulated as gelatin capsules or tablets containing from 1 mg to 1000 mg of active ingredient for oral administration, or as injectable preparations containing from 0.1 to 500 mg of active ingredient, or else as suppositories, ointments, creams, gels, aerosol preparations or eye lotions.

In human and animal therapeutics, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels or aerosol preparations, can be envisaged.

As will be clearly apparent from the pharmacological tests given at the end of the description, the compounds according to the invention can be administered in human therapeutics for the above-mentioned indications, orally in the form of tablets or gelatin capsules containing from 1 mg to 1000 mg of active ingredient, or parenterally in the form of injectable preparations containing from 0.1 mg to 500 mg of active ingredient, in one or more daily dosage units for an adult with an average weight of 60 to 70 kg.

In animal therapeutics, the daily dose which can be used is between 0.1 and 100 mg per kg.

Further characteristics and advantages of the invention will be understood more clearly from the following description of some Examples, which in no way imply a limitation but are given by way of illustration.

Example 1

β-D-Ribofuranuronamido-1-(6-chloro-9H-purin9-yl)-N-cyclopropyl-1-deoxy-2,3-O-(1-methylethylidene)

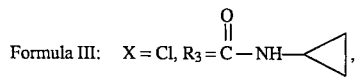

Formula III:  $X = Cl$, $R_3 = \overset{O}{\overset{\|}{C}} - NH-\triangleleft$, $R_9$, $R_{10}$ = isopropylidene 20 g of 2',3'-O-isopropylidene-6-chloropurine-5'-uronic acid, prepared according to SCHMIDT R. R. and FRITZ H. J., Chem. Ber. 1970, 103(6), 1867–71, in 500 ml of anhydrous CHCl$_3$ stabilized with amylene, are refluxed for 5 h in the presence of 86 ml of SOCl$_2$ and 10 ml of anhydrous DMF.

The excess SOCl$_2$ and the solvents are distilled. The residue is taken up with 200 ml of anhydrous chloroform and added dropwise, under nitrogen, to a mixture of 150 ml of CHCl$_3$ and 41 ml of cyclopropylamine, cooled to 5° C. beforehand. The temperature of the reaction mixture is kept below 10° C. during the addition of the acid chloride.

The mixture is left to react for a further 30 min and then washed 3 times with a dilute HCl solution and then with a sodium bicarbonate solution. A final washing with water, followed by drying and evaporation of the solvent, gives 26.3 g of a brown oil.

Purification by chromatography on silica gel (eluent: CH$_2$Cl$_2$ 90%/acetone 10%) gives 15.7 g of β-D-ribofuranuronamido-1-(6-chloro-9 H-purin-9-yl)-N-cyclopropyl-1-deoxy-2,3-O-(1-methylethylidene) in the form of an amorphous solid.

The compounds of Examples 2 to 6 were prepared by the procedure of Example 1 using the appropriate amines.

Example 2

β-D-Ribofuranuronamido-1-(6-chloro-9H-purin-9-yl)-1-deoxy-N-ethyl-2,3-O-(1-methylethylidene)

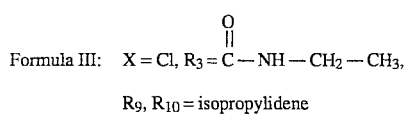

Formula III:  X = Cl, R$_3$ = C—NH—CH$_2$—CH$_3$,

R$_9$, R$_{10}$ = isopropylidene

A yellowish oil purified by chromatography on silica gel (eluent: chloroform 95%/methanol 5%) to give a solid melting at 91° C.

Example 3

β-D-Ribofuranuronamido-1-(6-chloro-9H-Purin-9-yl)-1-deoxy—N-(1-hydroxy-2-methylpropan-2-yl)-2,3-O-(1-methylethylidene)

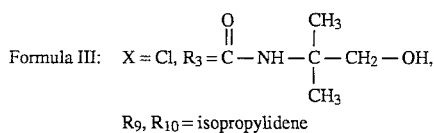

Formula III:  X = Cl, R$_3$ = C—NH—C—CH$_2$—OH,

R$_9$, R$_{10}$ = isopropylidene

A brown oil purified by chromatography on silica gel (eluent: chloroform 90%/methanol 10%).

Example 4

β-D-Ribofuranuronamido-1-(6-chloro-9H-purin-9-yl)-1-deoxy-N-isopropyl-2,3-O-(1-methylethylidene)

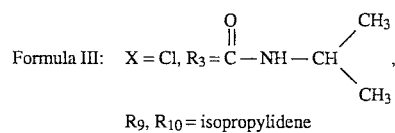

Formula III:  X = Cl, R$_3$ = C—NH—CH(CH$_3$)$_2$,

R$_9$, R$_{10}$ = isopropylidene

An orange oil purified by chromatography on silica gel (eluent: CHCl$_3$ 90%/acetone 10%).

Example 5

β-D-Ribofuranuronamido-1-(6-chloro-9H-Purin9-yl)-1-deoxy—N-(2-methoxyethyl)-2,3 -O-(1-methylethylidene)

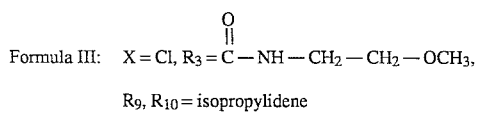

Formula III:  X = Cl, R$_3$ = C—NH—CH$_2$—CH$_2$—OCH$_3$,

R$_9$, R$_{10}$ = isopropylidene

A brown oil purified by chromatography on silica gel (eluent: chloroform 95%/methanol 5%).

Example 6

β-D-Ribofuranuronamido-1-(6-chloro-9H-purin-9-yl)-1-deoxy-N-(2-morpholinoethyl)-2,3 -O-(1-methylethylidene)

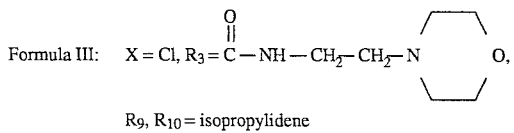

Formula III:  X = Cl, R$_3$ = C—NH—CH$_2$—CH$_2$—N(morpholino),

R$_9$, R$_{10}$ = isopropylidene

An amorphous solid obtained after purification by chromatography on silica gel (eluent: chloroform methanol 10%).

Example 7:

2-Amino-3-[(2,5-dimethylphenyl)methoxy]pyridine

Formula VIII: R$_1$=3-[(2,5-dimethylphenyl)methoxy], R$_2$=H

A solution of a mixture of 22 g of 2-amino-3-hydroxypyridine, 31 ml of 2,5-dimethylbenzyl chloride and 1.1 g of adogen 464 in 100 ml of aqueous NaOH (40%) and 100 ml of dichloromethane is stirred for 16 h at 25° C. The dichloromethane is separated off and the aqueous phase is diluted with 200 ml of water and extracted with dichloromethane (2×100 ml). The combined organic phases are washed with water, dried and concentrated to give 50.9 g of a brown solid. Purification by recrystallization from ethanol gives 28.5 g of 2-amino-3-[(2,5-dimethylphenyl)methoxy] pyridine.

Melting point: 133° C.

Example 8

2-Amino-3-(2-methoxyethoxy)pyridine

Formula VIII: R$_1$=3-(2-methoxyethoxy), R$_2$=H 22 g of 2-amino-3-hydroxypyridine are added in portions to a suspension of 8 g of ground NaOH in 200 ml of methanol, placed under nitrogen. After a quarter of an hour, the mixture is concentrated to dryness and the residue is taken up with 280 ml of DMSO. 20.8 ml of 2-bromoethyl methyl ether are added dropwise, the temperature of the reaction medium being prevented from exceeding room temperature. The mixture is stirred for 12 h at room temperature, the nitrogen atmosphere being maintained.

The reaction mixture is poured into 1600 ml of water and extracted with chloroform (4×200 ml). The combined organic phases are washed with water, dried and concentrated to give 23 g of an oil.

Purification by chromatography on silica gel (eluent: CHCl$_3$ 95%/isopropylamine 5%) gives 21.5 g of 2-amino-3-(2-methoxyethoxy)pyridine in the form of an oil.

The following compounds of Examples 9 to 12 were prepared by one or other of the procedures of Examples 7 and 8:

Example 9

2-Amino-3-(2-pyridylmethoxy)pyridine

Formula VIII: R$_1$=3-(2-pyridylmethoxy), R$_2$=H

Purified by chromatography on silica gel (eluent: chloroform 95%/methanol 5%).

Melting point: 98° C.

Example 10

2-Amino-3-(2-piperidinoethoxy)pyridine

Formula VIII: R$_1$=3-(2-piperidinoethoxy), R$_2$=H

Melting point: 104° C.

Example 11

2-Amino-3-(isopropoxy)pyridine
Formula VIII: $R_1$=3-isopropoxy, $R_2$=H
An oil purified by chromatography on silica gel (eluent: chloroform 95%/methanol 5%).

Example 12

2-Amino-3-(cyclopentoxy)pyridine
Formula VIII: $R_1$=3-cyclopentoxy, $R_2$=H
A greenish oil which crystallizes slowly.

Example 13

8-(Phenylmethoxy)imidazo[1,2-a]pyridine
Formula V: $R_1$=8-(phenylmethoxy), $R_2$=H
9 ml of chloroacetaldehyde (45% in water) and then 8.4 g of $NaHCO_3$ are added to a solution of 10 g of 2-amino-3-(phenylmethoxy)pyridine in 50 ml of 95% ethanol. The mixture is refluxed for 15 h.

The insoluble material is filtered off and washed with 95% ethanol. The mother liquors are concentrated, taken up with water and rendered alkaline with a 5% NaOH solution. After extraction with chloroform, the organic phases are washed with water and then dried and concentrated. The oil obtained is triturated in ether to give 9.4 g of 8-(phenylmethoxy)imidazo[1,2-a]pyridine in the form of a brown solid.

Melting point: 110° C.

The following compounds of Examples 14 to 20 were prepared by the above procedure of Example 13 using the appropriate α-halogenoketones:

Example 14

8-[(2,5-Dimethylphenyl)methoxy]imidazo[1,2-a]pyridine
Formula V: $R_1$=8-[(2,5-dimethylphenyl)methoxy], $R_2$=H
Melting point: 143° C.

Example 15

2-Methyl-8-[(2,5-dimethylphenyl)methoxy]imidazo[1,2-a]pyridine
Formula V: $R_1$=8-[(2,5-dimethylphenyl)methoxy], $R_2$=2—$CH_3$
An oil purified by chromatography on silica gel (eluent: chloroform 95%/isopropylamine 5%) and crystallizing slowly.

Example 16

8-(2-Methoxyethoxy)imidazo[1,2-a]pyridine
Formula V: $R_1$=8-(2-methoxyethoxy), $R_2$=H
An oil purified by chromatography on silica gel (eluent: chloroform 95%/isopropylamine 5%) and crystallizing slowly.
Melting point: 80° C.

Example 17

8-(2-Pyridylmethoxy)imidazo[1,2-a]pyridine
Formula V: $R_1$=8-(2-pyridylmethoxy), $R_2$=H
An oil used as such without purification.

Example 18

8-(2-Piperidinoethoxy)imidazo[1,2-a]pyridine
Formula V: $R_1$=8-(2-piperidinoethoxy), $R_2$=H
A yellowish oil purified by chromatography on silica gel (eluent: chloroform 95%/isopropylamine 5%) and crystallizing slowly.

Example 19

8-(Isopropoxy)imidazo[1,2-a]pyridine
Formula V: $R_1$=8-isopropoxy, $R_2$=H
A brown oil used as such without purification.

Example 20

8-(Cyclopentoxy)imidazo[1,2-a]pyridine
Formula V: $R_1$=8-cyclopentoxy, $R_2$=H
Melting point: 94° C.

Example 21

3-(2-Aminoethyl)-8-[(2,5-dimethylphenyl)methoxy]imidazo[1,2-a]pyridine hydrochloride
Formula II: $R_1$=8-[(2,5-dimethylphenyl)methoxy], $R_2$=H a) Preparation of 3-[(dimethylamino)methyl]-8-[(2,5-dimethylphenyl)methoxy]imidazo[1,2-a]pyridine hydrochloride A mixture of 26.6 g of [(2,5-dimethylphenyl)methoxy]imidazo[1,2-a]pyridine prepared in Example 14, 9.1 g of dimethylamine hydrochloride, 3.4 g of paraformaldehyde and 100 ml of methanol is refluxed for 2 h. The solution is concentrated to ⅔ of its volume. 10 ml of concentrated HCl are added at room temperature and the mixture is stirred for several hours. A precipitate gradually appears. This is filtered off and washed with ether to give 37.9 g of 3-[(dimethylamino)methyl]-8-[(2,5-dimethylphenyl)methoxy]imidazo[1,2-a]pyridine hydrochloride.

Melting point: 220° C.

b) Preparation of 8-[(2,5-dimethylphenyl)methoxy]-3-[(trimethylammonio)methyl]imidazo[1,2-a]pyridine iodide 37.9 g of the hydrochloride prepared as above are dissolved in 300 ml of water (with gentle heating if necessary). The pH is brought to 11–12 by the addition of a 50% NaOH solution. The mixture is cooled to 0° C. and extracted with dichloromethane. The combined organic phases are washed with a solution of $H_2O$/NaCl, dried and concentrated to give 32.3 g of a brown oil.

The oil obtained above is dissolved in 150 ml of ethanol. The solution is cooled to 0° C. and 6.8 ml of $ICH_3$ are added dropwise.

The mixture is stirred overnight at room temperature. The solid obtained is filtered off and rinsed with ethanol and then ether to give 38.4 g of 8-[(2,5-dimethylphenyl)methoxy]-3-[(trimethylammonio)methyl]imidazo[1,2-a]pyridine iodide.

Melting point: 227° C.

c) Preparation of 3-(cyanomethyl)-8-[(2,5-dimethylphenyl)methoxy]imidazo[1,2-a]pyridine A mixture of 204.5 g of the quaternary ammonium compound prepared in Example 21b), 1200 ml of DMF and 34 g of NaCN is heated in a water bath for 6 h, with stirring. It is cooled to room temperature and then poured into 3 l of a water/ice mixture and extracted with chloroform. The combined organic phases are washed with water, dried and concentrated to give 112.9 g of a brown solid.

Melting point: 164° C.

Purification by chromatography on silica gel (eluent: chloroform 90%/methanol 10%) gives 73.7 g of 3-(cyanomethyl)-8-[(2,5-dimethylphenyl)methoxy]imidazo[1,2-a]pyridine in the form of a cream-colored solid.

Melting point: 168° C.

d) Preparation of 3-(2-aminoethyl)-8-[(2,5-dimethylphenyl)methoxy]imidazo[1,2-a]pyridine Formula II: $R_1$=8-[(2,5-dimethylphenyl)methoxy], $R_2$=H A mixture of 40 g of the cyanomethyl derivative obtained according to Preparation 21c) above in 500 ml of ammoniacal methanol is catalytically reduced in the presence of Raney Ni for 8 h, in an autoclave, under a hydrogen pressure of 90 kg and at 100° C. The reaction mixture is filtered on Célite. The organic phase is concentrated and then taken up with chloroform. The insoluble material is removed and the organic phase is concentrated to give 51.2 g of an oil.

The oil is taken up with 150 ml of isopropanol and acidified with 26 ml of an isopropanol/HCl solution (5.6N). The solid obtained is filtered off and rinsed with isopropanol and then ether to give 33.8 g of 3-(2-aminoethyl)-8-[(2,5-dimethylphenyl)methoxy] imidazo[1,2-a]pyridine hydrochloride.

Melting point: 229° C.

Example 22

3-(2-Aminoethyl)-8-(phenylmethoxy)imidazo[1,2-a]pyridine

Formula II: $R_1$=8-(phenylmethoxy), $R_2$=H a) Preparation of 3-formyl-8-(phenylmethoxy)imidazo[1,2-a]pyridine A mixture of 10 g of 8-(phenylmethoxy)imidazo[1,2-a]pyridine prepared in Example 13 and 31 ml of DMF is cooled to 10° C. 4.7 ml of $POCl_3$ are added dropwise. The mixture is allowed to return to room temperature and then heated at 100° C. for 30 min. After cooling, 85 ml of $H_{20}$ and 16 ml of NaOH (50%) are added. The mixture is heated at 90° C. for 1 h and then allowed to cool. The solid obtained is filtered off and then washed with water until the pH of the mother liquors is neutral. This gives 8.8 g of 3-formyl-8-(phenylmethoxy)imidazo[1,2-a]pyridine.

Melting point: 167° C.

b) Preparation of 3-(2-nitroethenyl)-8-(phenylmethoxy)imidazo[1,2-a]pyridine

The aldehyde prepared above (5 g) is reacted with 40 ml of nitromethane and 1 g of ammonium acetate. The mixture is refluxed for 1 h. The solid obtained is washed with water and then purified by chromatography on silica gel (eluent: dichloromethane 95%/acetone 5%) to give 1 g of the expected 3-(2-nitroethenyl)-8-(phenylmethoxy)imidazo[1,2-a]pyridine (melting at 204° C.) and 1.5 g of the starting aldehyde, which can be recycled.

c) Preparation of 3-(2-aminoethyl)-8-(phenylmethoxy)imidazo[1,2-a]pyridine

Formula II: $R_1$=8-phenylmethoxy, $R_2$=H

The compound obtained in Example 22b) is dissolved (3 g) in 200 ml of hot THF. This mixture is then added dropwise to a suspension of 3 g of $LiAlH_4$ in 50 ml of THF. When the addition has ended, the mixture is refluxed for 1 h 30 min. The excess $LiAlH_4$ is destroyed at 0° C. with an aqueous $Na_2SO_4$ solution. The mixture is filtered on Célite and the material on the filter is rinsed with ethyl acetate. Concentration of the organic phases gives 3-(2-aminoethyl)-8-(phenylmethoxy)imidazo[1,2-a]pyridine in the form of a brown oil, which is purified by chromatography on silica gel (eluent: $CHCl_3$ 95%/isopropylamine 5%).

The compounds of Examples 23 to 26 were prepared by the procedure of Example 21 or 22.

Example 23

3-(2-Aminoethyl)-2-methyl-8-[(2,5-dimethylphenyl)methoxy]imidazo[1,2-a]pyridine

Formula II: $R_1$=8-[(2,5-dimethylphenyl)methoxy], $R_2$=2-$CH_3$

A brown oil purified after treatment with a solution of hydrochloric acid in isopropanol (6N).

Melting point of the hydrochloride: 272° C.

Example 24

3-(2-Aminoethyl)-8-(2-methoxyethoxy)imidazo[1,2-a]pyridine

Formula II: $R_1$=8-(2-methoxyethoxy), $R_2$=H

A brown oil purified by chromatography on silica gel (eluent: chloroform 90%/isopropylamine 10%).

Example 25

3-(2-Aminoethyl)-8-(cyclopentoxy)imidazo[1,2-a]pyridine

Formula II: $R_1$=8-cyclopentoxy, $R_2$=H

A brown oil used as such without purification.

Example 26

3-(2-Aminoethyl)-8-(isopropoxy)imidazo[1,2-a]pyridine

Formula II: $R_1$=8-isopropoxy, $R_2$=H

A brown oil used as such without purification.

Example 27

β-D-Ribofuranuronamido-N-cyclopropyl-1-deoxy-1-[6-[[2-[8-(phenylmethoxy)imidazo[1,2-a]pyridin-3-yl]ethyl]amino]-9H-purin-9-yl]-2,3-O-(1-methylethylidene)

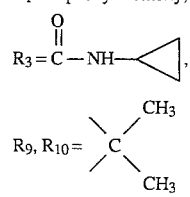

Formula IV: $R_1$ = 8-phenylmethoxy, $R_2$ = H, $R_3 = C(=O)-NH-\triangleleft$, $R_9, R_{10} = C(CH_3)(CH_3)$ A mixture of 7.3 g of 3-(2-aminoethyl)-8(phenylmethoxy)imidazo[1,2-a]pyridine prepared in Example 22, 7.9 g of β-D-ribofuranuronamido-1-(6-chloro-9 H-purin-9-yl)-N-cyclopropyl-1-deoxy-2,3-O-(1-methylethylidene) prepared in Example 1, 100 ml of ethanol and 9.6 ml of triethylamine is refluxed for 7 h under a nitrogen atmosphere. It is concentrated and then taken up with chloroform, washed with water and an aqueous solution of NaCl, dried and concentrated to give 14 g of an amorphous solid.

Purification by chromatography on silica gel. (eluent: chloroform 95%/methanol 5%) gives 12.8 g of β-D-ribofuranuronamido-N-cyclopropyl-1-deoxy-1-[6-[[2-(phenylmethoxy)imidazo[1,2-a]pyridin-3-yl]ethyl]amino]-9H-purin-9-yl]-2,3-O-(1-methylethylidene) in the form of an amorphous white solid.

The compounds of Examples 28 to 32 were prepared by reacting differently substituted 3-(2-aminoethyl)imidazo[1,2-a]pyridines with the appropriate 6-chloropurines by the procedure of Example 27.

Example 28

β-D-Ribofuranuronamido-N-cyclopropyl-1-deoxy-1-[6-[[2-[[8-(2,5-dimethylphenyl)methoxy]imidazo[1,2-a]pyridin-3-yl]ethyl] amino]-9H-purin-9-yl]-2,3—O-(1-methylethylidene)

Formula IV: $R_1 = 8\text{-}[(2,5\text{-dimethylphenyl})\text{methoxy}]$, $R_2 = H$,

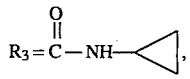

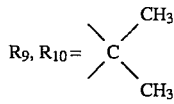

Example 29

β-D-Ribofuranuronamido-N-cyclopropyl-1-deoxy-1-[6-[[2-[8-(2-methoxyethoxy)imidazo[1,2-a]pyridin-3-yl]ethyl] amino]-9H-purin-9-yl]-2,3-O-(1-methylethylidene)

Formula IV: $R_1 = 8\text{-}(2\text{-methoxyethoxy})$, $R_2 = H$,

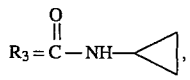

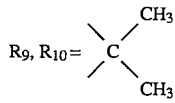

Example 30

β-D-Ribofuranuronamido-N-cyclopropyl-1-deoxy-1-[6-[[2-[[8-(2,5-dimethylphenyl)methoxy]-2-methylimidazo[1,2-a]pyridin-3-yl]ethyl]amino]-9H-purin-9-yl]-2,3-O-(1-methylethylidene)

Formula IV: $R_1 = 8\text{-}[(2,5\text{-dimethylphenyl})\text{methoxy}]$, $R_2 = 2\text{-}CH_3$,

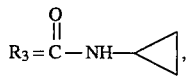

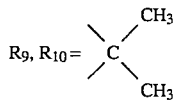

Example 31

β-D-Ribofuranuronamido-N-cyclopropyl-1-deoxy-1-[6-[[2-[8-(cyclopentoxy)imidazo[1,2-a]pyridin-3-yl]ethyl]amino]-9H-purin-9-yl]-2,3-O-(1-methylethylidene)

Formula IV: $R_1 = 8\text{-cyclopentoxy}$, $R_2 = H$,

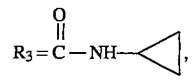

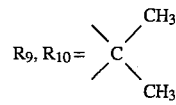

Example 32

β-D-Ribofuranuronamido-N-cyclopropyl-1-deoxy-1-[6-[[2-[8-(isopropoxy) imidazo[1,2-a]pyridin-3-yl]ethyl] amino]-9H-purin-9-yl]-2,3-O-(1-methylethylidene)

Formula IV: $R_1 = \text{isopropoxy}$, $R_2 = H$,

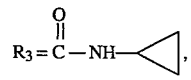

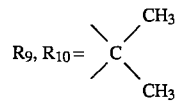

Example 33

β-D-Ribofuranuronamido-N-cyclopropyl-1-deoxy-1-[6-[[2-[8-(phenylmethoxy)imidazo[1,2-a]pyridin-3-yl] ethyl] amino]-9H-purin-9-yl]

Formula I: $R_1 = 8\text{-phenylmethoxy}$, $R_2 = H$,

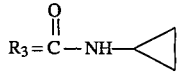

A mixture of 13 g of the β-D-ribofuranuronamide of Example 27 and 378 ml of 50% formic acid is heated at 70° C. for 1 h 15 min. The formic acid is removed by evaporation. The residue is taken up with water and concentrated. This operation is repeated once and the residue is then taken up with methanol and concentrated again. The concentrate is taken up with water and triturated to give 9.6 g of a white solid.

Melting point: 191° C.

Recrystallization from methoxyethanol gives 7.4 g of β-D-ribofuranuronamido-N-cyclopropyl-1-deoxy-1-[6-[[2-[8-(phenylmethoxy)imidazo[1,2-a]pyridin-3-yl]ethyl]amino]-9H-purin-9-yl].

Empirical formula: $C_{29}H_{30}N_8O_5 \cdot 0.3H_2O$.

Melting point: 177° C.

The compounds of Examples 34 to 38 were prepared by the procedure of Example 33.

Example 34

β-D-Ribofuranuronamido-N-cyclopropyl-1-deoxy-1-[6-[[2-[[8-(2,5 -dimethylphenyl)methoxy]imidazo[1,2-a]pyridin-3-yl]ethyl]amino]-9H-purin-9-yl]

Formula I: $R_1$ = 8-[(2,5-dimethylphenyl)-methoxy], $R_2$ = H,

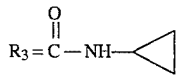

Purified by chromatography twice in succession on silica gel [eluent: (chloroform 90%/methanol 10%) and (chloroform 80%/methanol 20%) respectively].

Empirical formula: $C_{31}H_{34}N_8O_5.0.3H_2O$.
Melting point: 147° C.

Example 35

β-D-Ribofuranuronamido-N-cyclopropyl-1-deoxy-1-[6-[[2-[8-(2 -methoxyethoxy)imidazo[1,2-a]pyridin-3-yl]ethyl]amino]-9H-purin-9-yl]

Formula I: $R_1$ = 8-(2-methoxyethoxy), $R_2$ = H,

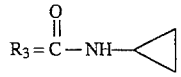

Purified by chromatography on silica gel (eluent: chloroform 90%/methanol 10%).

Empirical formula: $C_{25}H_{30}N_8O_6.0.2H_2O$.
Melting point: 174° C.

Example 36

β-D-Ribofuranuronamido-N-cyclopropy-1-deoxy-1-[6-[[2-[[8-(2,5-dimethylphenyl)methoxy]-2-methylimidazo[1,2-a]pyridin-3-yl]ethyl]amino]-9H-purin-9-yl]

Formula I: $R_1$ = 8-[(2,5-dimethylphenyl)-methoxy], $R_2$ = 2-CH$_3$,

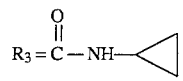

Purified by chromatography on silica gel (eluent: chloroform 90%/methanol 10%), followed by recrystallization from isopropanol.

Empirical formula: $C_{32}H_{36}N_8O_5.0.4H_2O$.
Melting point: 162° C.

Example 37

β-D-Ribofuranuronamido-N-cyclopropyl-1-deoxy-1-[6-[[2-[8-(cyclopentoxy)imidazo[1,2-a]pyridin-3-yl] ethyl] amino]-9H-purin-9-yl]

Formula I: $R_1$ = 8-cyclopentoxy, $R_2$ = H,

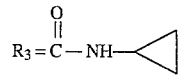

Purified by chromatography on silica gel (eluent: chloroform 90%/methanol 10%).

Empirical formula: $C_{27}H_{32}N_8O_5.0.9H_2O$.
Melting point: 162° C.

Example 38

β-D-Ribofuranuronamido-N-cyclopropyl-1-deoxy-1-[6-[[2-[8-(isopropoxy)imidazo[1,2-a]pyridin-3-yl]ethyl]amino]-9H-purin-9-yl]

Formula I: $R_1$ = 8-isopropoxy, $R_2$ = H,

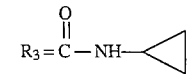

Purified by chromatography on silica gel (eluent: chloroform 80%/methanol 20%) and recrystallized from acetonitrile.

Empirical formula: $C_{25}H_{30}N_8O_5$.
Melting point: 151° C.

Example 39

$N^6$-2-[[8-(2,5-Dimethylphenyl)methoxy]imidazo[1,2-a]pyridin-3-yl]ethyladenosine Formula I: $R_1$=8-[(2,5-dimethylphenyl)methoxy], $R_2$=H, $R_3$=CH$_2$OH A mixture of 4.8 g of the hydrochloride prepared in Example 21d), 4.5 g of 6-chloroadenosine, 5.3 ml of triethylamine and 100 ml of ethanol is refluxed for 7 h. The resulting solution is concentrated, taken up with CHCl$_3$ and washed with water and a saturated solution of H$_2$O/NaCl. The organic phase is dried and concentrated. The solid obtained is purified by chromatography on silica gel (eluent: CHCl$_3$ 90%/methanol 10%) Recrystallization from methanol gives 4.3 g of analytically pure $N^6$-2-[[8-(2,5 -dimethylphenyl)methoxy]imidazo[1,2-a]pyridin-3-yl]ethyladenosine.

Empirical formula: $C_{28}H_{31}N_7O_5.0.3H_2O$.
Melting point: 141° C.

PHARMACOLOGY

The pharmacological activity of the products of the Examples was evaluated by three different approaches: binding to adenosine receptors, demonstration of analgesic activity by the phenylbenzoquinone test, and demonstration of inhibitory activity on the cell proliferation induced by a growth factor in Balbc 3T3 fibroblasts.

I Procedure

1. Binding to adenosine receptors

Principle

The affinity of the products of the Examples for the rat central A1 and A2 adenosinergic receptors is determined by the competitive technique using a radioactive ligand specifically bound either to the A1 receptors ($[^3H]$ PIA) or to the A2 receptors ($[3H]$ NECA).

Method

Method of studying the A1 receptors
Membrane preparation

After the animal has been sacrificed by decapitation, the brain is quickly removed and washed in cold isotonic solution. The two hemispheres are separated and weighed and each of them is introduced into a polyallomer tube containing 25 volumes of cold homogenization buffer. Homogenization is effected using an Ultra-Turrax for 30 seconds. The ground material obtained is centrifuged at 1000 g for 10 minutes at 4° C.

The supernatant is centrifuged again at 48,000 g for 20 minutes at 4° C.

When this step is complete, the residue is taken up with 4 volumes of homogenization buffer, resuspended using a Vortex and homogenized with the Ultra-Turrax. Adenosine deaminase is then added at a rate of 1 U/ml of homogenate.

After this treatment, the homogenate is shaken for 30 minutes at room temperature and then centrifuged at 48,000 g for 30 minutes at 4° C.

The residue obtained is resuspended in 10 volumes of homogenization buffer and passed through the Ultra-Turrax for 20 seconds.

The homogenate prepared in this way is used for the competitive tests. It is kept at 4° C. if the studies take place the same day, or stored at –20° C.

Competitive test

After the homogenate has been thawed at room temperature, it is passed through a glass Potter homogenizer (6 manual to-and-fro movements, speed 6), diluted to 2/5 in incubation buffer and placed in a water bath thermostated at 4° C., with shaking, until the end of the experiment.

50 µl of $[^3H]$ PIA at 100 nM, i.e. 2.5 nM in the final reaction medium allowing for the 1/40 dilution, and 50 µl of the product of the Example at the concentrations considered ($10^{-5}$M and $10^{-7}$M) are introduced into the reaction tubes. The reaction is initiated by the addition of 1 ml of homogenate and 900 µl of incubation buffer.

The tubes are shaken and incubated in a water bath at 20° C. for 30 minutes. When the incubation is complete, the contents of the tubes are filtered on Whatman GF/B paper. Each tube is washed twice with 2 ml of rinsing buffer and then the filters themselves are rinsed with 3 ml of this same buffer.

The filters are then transferred to counting flasks and 10 ml of liquid scintillator (Ready Solv HP/b, Beckman) are added.

After they have been shaken, the flasks are stored in a refrigerator overnight and the radioactivity is then determined in a liquid scintillation counter.

3 tests are performed for each concentration studied. The non-specific binding of the $[^3H]$ PIA is assessed by measuring the amount of radioactivity retained on the filter in the presence of $10^{-5}$M phenylisopropyladenosine (PIA). The value of the non-specific binding is systematically subtracted from that of the tests.

Method of studying the A2 receptors
Membrane preparation

After decapitation of the animal, the brain is quickly removed and washed in cold isotonic solution. The two hemispheres are separated and the striatum is removed from each of them (Bruns et al., 1986), weighed and introduced into a polyallomer tube containing 10 volumes of cold homogenization buffer. The tissue is homogenized with an Ultra-Turrax for 30 seconds. The ground material is centrifuged at 50,000 g for 10 minutes at 4° C.

The residue obtained is resuspended in 10 volumes of homogenization buffer using a Vortex and homogenized with the Ultra-Turrax.

Adenosine deaminase is then added at a rate of 1 U/ml of homogenate. The homogenate treated in this way is shaken at room temperature for 30 minutes.

When the incubation is complete, the homogenate is centrifuged at 50,000 g for 10 minutes at 4° C.

The residue is taken up with 5 volumes of cold homogenization buffer and passed through the UltraTurrax and the homogenate prepared in this way is finally frozen at –70° C.

Competitive test

After the homogenate has been thawed at room temperature, 15 volumes of incubation buffer are added. The homogenate is shaken on a Vortex, passed through a glass Potter homogenizer (6 to-and-fro movements, speed diluted to 1/10 in incubation buffer and finally placed in a water bath thermostated at 4° C., with shaking, until the end of the experiment.

50 µl of $[^3H]$ NECA at 160 nM, i.e. 4 nM in the final reaction medium allowing for the 1/40 dilution, and 50 µl of the product of the Example at the concentrations considered ($10^{-5}$M and $10^{-7}$M) are introduced into the reaction tubes. The reaction is initiated by the addition of 1 ml of homogenate and 900 µl of incubation buffer. The procedure is similar for all the compounds studied.

The tubes are shaken and incubated in a water bath at 25° C. for 60 minutes. When the incubation is complete, the contents of the tubes are filtered on Whatman GF/B paper. Each tube is washed twice with 2 ml of rinsing buffer and then the filters themselves are rinsed with 3 ml of this same buffer before being transferred to counting flasks.

10 ml of liquid scintillator (Ready Solv HP/b, Beckman) are added to all the flasks. These are shaken and stored in a refrigerator overnight. The radioactivity is determined in a liquid scintillation counter.

3 tests are performed for each concentration studied. The non-specific binding of the $[^3H]$ NECA is determined by measuring the amount of radioactivity retained on the filter in the presence of 5 µM N-ethylcarboxamidoadenosine (NECA). The value of the non-specific binding is systematically subtracted from that of the tests.

Treatment of the data

The results are expressed for each product in the form of the percentage displacement (n=3) of the labeled radioligand at concentrations of $10^{-5}$M and $10^{-7}$M.

2. Phenylbenzoquinone test

Method

The intraperitoneal injection of phenylbenzoquinone causes twisting and stretching movements in mice. Analgesics prevent or reduce this syndrome, which can be considered as the exteriorization of diffuse abdominal pain.

A 0.02% solution of phenylbenzoquinone in water is administered in a volume of 1 ml/100 g.

The products of the Examples are administered orally one hour before the injection of phenylbenzoquinone.

The stretching and twisting movements are counted for each mouse over an observation period of 5 minutes.

II Results

The results of the experiments demonstrating the affinity of the products of the Examples for adenosine receptors, and their analgesic properties, are presented in Tables 1 and 2 respectively.

TABLE 1

| Product of | % displacement of the radioligand | | | |
|---|---|---|---|---|
| | A1 | | A2 | |
| | 1E–5M | 1E–7M | 1E–5M | 1E–7M |
| Example 33 | 94 | 45 | 89 | 13 |
| Example 34 | 90 | 41 | 86 | 15 |
| Example 35 | 100 | 98 | 80 | 1 |
| Example 36 | 93 | 29 | 84 | 12 |
| Example 37 | 96 | 44 | 80 | 6 |

TABLE 2

| Product of | Phenylbenzoquinone test % inhibition at 30 mg/kg p.o. |
|---|---|
| Example 33 | 39 |
| Example 34 | 57 |
| Example 35 | 25 |
| Example 36 | 63 |
| Example 37 | 57 |

Measurement of the inhibition of the cell proliferation induced by a growth factor in Balbc smooth 3T3 fibroblasts

I. Principle

Inhibition of the cell proliferation induced by a growth factor (for example PDGF) is evaluated by measuring the incorporation of $^3$H-thymidine into Balbc 3T3 fibroblasts.

II. Procedure

The Balbc 3T3 fibroblasts are cultivated at 37° C. with 5% of $CO_2$ up to the point of subconfluence and are then placed for 18 hours under rest conditions in a serum-impoverished medium. They are subsequently pretreated for one hour with the test molecule ($10^{-5}$M and/or $10^{-6}$M) and then stimulated for 22 hours with a growth factor (for example PDGF). $^3$H-Thymidine is incorporated over the last 2 hours. All these steps are performed at 37° C. with 5% of $CO_2$.

The reaction is terminated by sucking off the reaction medium, detaching the cells and then filtering the lyzed cells through glass fiber filters.

III. Expression of the Results

The results are expressed as the percentage inhibition of the stimulation of $^3$H-thymidine incorporation induced by the growth factor.

The results obtained, which are presented in Table 3, show that the compounds of formula (I) have a powerful inhibitory effect on the proliferation of Balbc 3T3 fibroblasts stimulated by PDGF.

TABLE 3

| Product of | % inhibition of the incorporation of $^3$H-thymidine stimulated by PDGF | |
|---|---|---|
| | 1E–5M | 1E–6M |
| Example 34 | | 72 |
| Example 36 | | 80 |
| Example 37 | 63 | |

III Toxicology

The tolerance of the products of the Examples described was assessed in mice after oral administration. It was found to be good up to a dose of 300 mg/kg.

IV Conclusion

The products of the Examples described in the present invention possess particularly valuable analgesic properties. These same compounds also have a powerful inhibitory effect on the proliferation of smooth muscle cells.

What is claimed is:

1. An adenosine compound of formula (I):

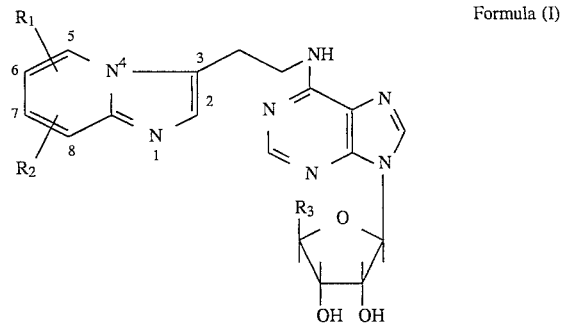

Formula (I)

in which:

$R_1$ and $R_2$, which can be located in the 2-, 5-, 6-, 7- or 8-position of the imidazopyridine, independently are:
a hydrogen atom,
a lower alkyl radical having 1 to 6 carbon atoms,
a halogen atom,
a radical $O-(CH_2)_n-R_4$,
in which n is an integer from 0 to 5 and $R_4$ is the hydrogen atom, a lower alkyl radical having 1 to 6 carbon atoms, a $C_3$–$C_7$-cycloalkyl radical, a lower O-alkyl radical having 1 to 6 carbon atoms, a phenyl radical which is unsubstituted or substituted by one to four identical or different substituents selected from a halogen atom or a lower alkyl radical having 1 to 6 carbon atoms, or a pyridyl radical, or
a phenyl radical; and $R_3$ is:
a group $-CO-NHR_5$,
in which $R_5$ is a lower alkyl radical having 1 to 6 carbon atoms, a $C_3$–$C_7$-cycloalkyl radical, a radical $-(CH_2)_m-OR_6$ or a radical $-(CH_2)_m-NR_7R_8$, in which m is an integer from 2 to 5, $R_6$ is the hydrogen atom or a lower alkyl radical having 1 to 6 carbon atoms and $R_7$ and $R_8$ simultaneously are a lower alkyl radical having 1 to 6 carbon atoms or form, together with the nitrogen atom to which they are attached, a heterocycle selected from morpholine, piperidine or pyrrolidine, or
a group CH₂OH,
and its addition salts, in particular the pharmaceutically acceptable addition salts.

2. A compound of formula (I) according to claim 1 wherein:

R₁ and R₂, which can be located in the 2- or 8-position of the imidazopyridine, independently are:
a hydrogen atom,
a lower alkyl radical having 1 to 6 carbon atoms,
a halogen atom or
a radical O—(CH₂)ₙ—R₄,
in which n is an integer from 0 to 2 and R₄ is a lower alkyl radical having 1 to 6 carbon atoms, a C₃C₇-cycloalkyl radical, a lower O-alkyl radical having 1 to 6 carbon atoms or a phenyl radical which is unsubstituted or substituted by one or two lower alkyl radicals having 1 to 6 carbon atoms; and R₃ is:
a group —CO—NHR₅,
in which R₅ is a lower alkyl radical having 1 to 6 carbon atoms, a C₃-C₇-cycloalkyl radical, a radical —CH₂—CH₂—O—R₆, in which R₆ is a lower alkyl radical having 1 to 6 carbon atoms, or a 2-morpholinoethyl radical, or
a group —CH₂OH,
and its addition salts, in particular the pharmaceutically acceptable addition salts.

3. A compound according to claim 1 wherein R₁ is selected from a phenylmethoxy group, a (2,5-dimethylphenyl)methoxy group, a 2-methoxyethoxy group, a cyclopentoxy group or an isopropoxy group.

4. A compound according to claim 1 wherein R₂ is the hydrogen atom or a methyl radical.

5. A compound according to claim 1 wherein R₃ is an N-cyclopropylcarboxamide radical.

6. A compound according to claim 1 which is selected from the derivatives of the formulae:

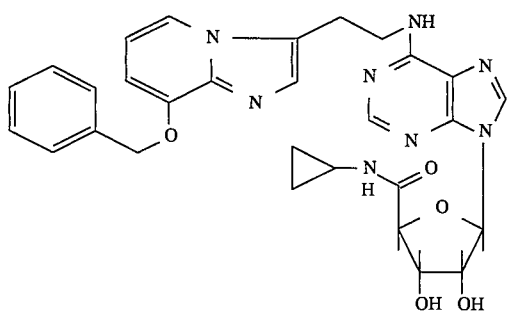

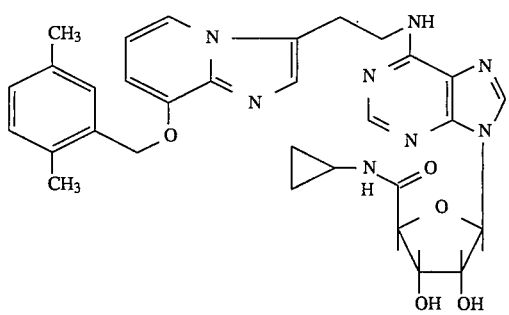

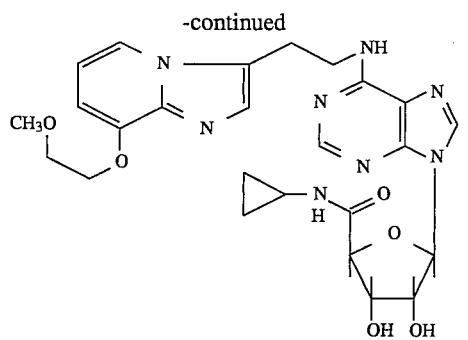

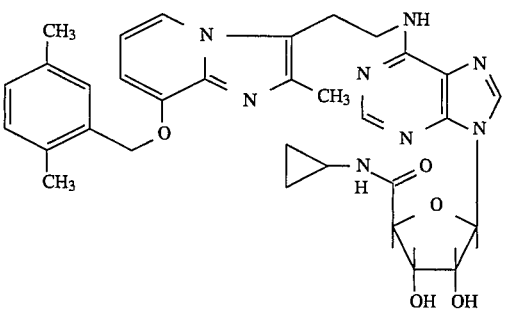

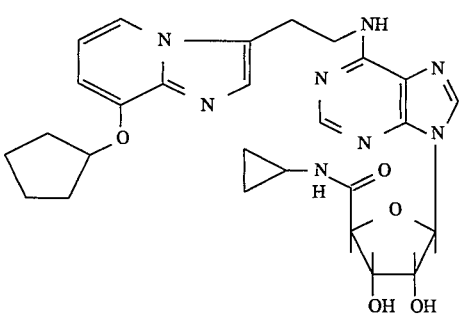

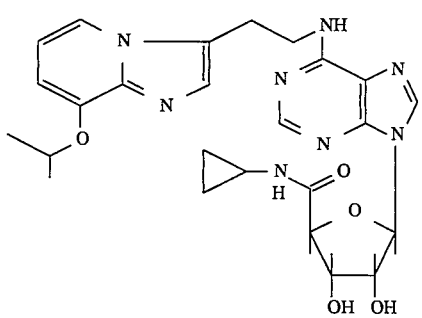

7. A pharmaceutical composition which comprises a pharmaceutically effective amount of a compound of formula (I) as defined in claim 1, or one of its pharmaceutically acceptable addition salts, incorporated in a pharmaceutically acceptable excipient, vehicle or carrier.

8. A pharmaceutical composition as claimed in claim 7, which is formulated as gelatin capsules or tablets containing from 1 to 1000 mg of active ingredient.

9. A pharmaceutical composition as claimed in claim 7, which is formulated as injectable preparations containing from 0.1 to 500 mg of active ingredient.

* * * * *